(12) United States Patent
Dietzen et al.

(10) Patent No.: US 6,703,431 B2
(45) Date of Patent: Mar. 9, 2004

(54) FLEXIBLE OPEN-CELLED MICROCELLULAR POLYMER FOAMS

(75) Inventors: Franz-Josef Dietzen, Hassloch (DE); Hans-Joachim Hähnle, Neustadt (DE); Serguei Evsioukov, Ludwigshafen (DE); Gunnar Schornick, Neuleiningen (DE); Gerd Ehrmann, Deidesheim (DE); Rüdiger Funk, Niedernhausen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 171 days.

(21) Appl. No.: 09/984,135

(22) Filed: Oct. 29, 2001

(65) Prior Publication Data

US 2002/0082311 A1 Jun. 27, 2002

(51) Int. Cl.$^7$ .................................................. C08J 9/00
(52) U.S. Cl. ........................ 521/149; 521/182; 604/358; 604/369
(58) Field of Search ................................ 521/149, 182, 521/79, 81, 139; 604/358, 369

(56) References Cited

U.S. PATENT DOCUMENTS

| 4,501,793 | A |   | 2/1985  | Sarada           |
|-----------|---|---|---------|------------------|
| 5,098,782 | A |   | 3/1992  | Hovis et al.     |
| 5,348,795 | A |   | 9/1994  | Park             |
| 5,387,050 | A |   | 2/1995  | Hovis et al.     |
| 5,618,853 | A |   | 4/1997  | Vonken et al.    |
| 5,698,144 | A |   | 12/1997 | Wilkes et al.    |
| 5,817,704 | A |   | 10/1998 | Shiveley et al.  |
| 6,093,752 | A | * | 7/2000  | Park et al.      |
| 6,174,471 | B1| * | 1/2001  | Park et al.      |
| 6,235,360 | B1| * | 5/2001  | Lanzani et al.   |
| RE37,780  | E | * | 7/2002  | Lanzani et al.   |
| 2002/0006976 | A1 | * | 1/2002 | Subramonian et al. |

FOREIGN PATENT DOCUMENTS

| DE | A 43 25 879   | 2/1995  |
|----|---------------|---------|
| EP | 0 754 632 A1  | 1/1997  |
| GB | 2 058 802     | 4/1981  |
| WO | WO 93/04113   | 3/1993  |
| WO | WO 96/00258   | 1/1996  |
| WO | WO 96/34038   | 10/1996 |
| WO | WO 98/56430   | 12/1998 |
| WO | WO 99/26670   | 6/1999  |
| WO | WO 00/53669   | 9/2000  |

* cited by examiner

*Primary Examiner*—Morton Foelak
(74) *Attorney, Agent, or Firm*—Keil & Weinkauf

(57) ABSTRACT

Flexible open-celled microcellular foams based on thermoplastic polymers are useful for fluid-absorbent hygiene articles.

5 Claims, No Drawings

FLEXIBLE OPEN-CELLED MICROCELLULAR POLYMER FOAMS

This invention relates to flexible open-celled microcellular polymer foams and to the use of such foams for producing fluid-absorbent hygiene articles. For hygiene articles such as infant diapers, incontinence products, sanitary protection articles or else wound contact materials and secondary wound dressings to function reliably, three functions have to be performed reliably:

Acquisition of body fluid
Uniform distribution of acquired fluid
Pressure-resistant storage of fluid.

Existing hygiene articles generally perform the last function reliably by means of superabsorbent polymers. Yet the continuing trend toward thinner and thinner hygiene articles requires that the materials hitherto used to accomplish acquisition and distribution (cellulose fluff) have to be replaced by other materials. Open-celled foams have been determined to be of particular interest here. In addition to the open-celled character, they have to be soft and flexible and have a hydrophilic surface to ensure rapid wetting by the aqueous body fluids.

It is known, for example from WO 99/26670, that such foams can be produced in a cell size of 0.01 to 0.1 mm from water-soluble polymers, for example carboxymethylcellulose, sodium polyacrylate or polyethylene oxide, by freeze drying the aqueous polymer solution and recovering the foam by heating. However, this is an extremely complicated process which presents serious process control problems.

WO 93/04113 discloses treating polyurethane foams for the production of hygiene articles with aqueous salt solutions to form a hydrophilic surface layer containing calcium chloride for example. This process too is fairly complicated, since large amounts of water have to be handled and then evaporated again.

DE-A 43 25 879 describes the production of open-celled foam sheets, including on the basis of polyolefins, by foam extrusion. The open-celled character is achieved by adding foreign polymers at extrusion and by raising the melt temperature. The cell size is said to be less than 1 mm, especially less than 0.4 mm. However, nowhere does it say how to generate cells whose average diameter is less than 0.1 mm. The examples feature the production of polystyrene foam using butane or a halogenated hydrocarbon as the blowing agent. The foams can be used in the packaging and building construction sectors or as insulation materials with no mention of utility as hygiene articles.

U.S. Pat. No. 5,098,782 and U.S. Pat. No. 5,387,050 describe the production of open-celled foams by foam extrusion of a mixture of LDPE and another polymer, for example EVA. Nothing is said about cell size or utility as hygiene articles.

U.S. Pat. No. 5,348,795 describes the production of open-celled polypropylene foams for cushioning and packaging purposes. The open-celled character is achieved by adapting the foaming temperature. Cell sizes in the range from 0.1 to 2.0 mm are reported in the examples.

WO 96/00258 describes open-celled polystyrene foams as roof insulation materials. The average cell size can be between 0.08 and 1.2 mm.

WO 96/34038 describes the production of vacuum insulation panels from polystyrene foams having a medium cell diameter of less than 0.07 mm.

EP-A 754 632 describes packaging trays produced from polystyrene foam sheeting having a cell diameter of between 0.1 and 1.5 mm.

It is an object of the present invention to provide flexible open-celled microcellular foams based on olefin polymers or thermoplastic polyesters and having an average cell diameter of less than 0.1 mm. It is a further object to develop flexible open-celled foams which are useful for fluid-absorbing hygiene articles and are producible by simple processes.

We have found that this object is achieved by flexible open-celled microcellular foams based on olefin polymers or thermoplastic polyesters, characterized by:

an open-cell content of more than 40%, preferably more than 50%, a density of less than 300 g/l, preferably of from 20 to 200 g/l, and an average cell diameter of less than 0.1 mm, preferably less than 0.08 mm.

To obtain flexible foams, appropriate polymers have to be used as starting materials.

Suitable are olefin polymers, such as polyethylene and polypropylene, and also copolymers of ethylene and propylene with each other and with minor amounts of vinyl acetate, butadiene, acrylic ester or acrylic acid. Particular preference is given to a copolymer of ethylene and from 5 to 30% by weight of vinyl acetate (EVA). Also suitable are thermoplastic polyesters, such as polyethylene terephthalate, polybutylene terephthalate, polyethylene glycol terephthalate and a biodegradable copolyester of terephthalic acid, adipic acid and butanediol. Mixtures of the polymers mentioned are also suitable.

To produce the foams of the invention, the polymers are melted in an extruder and then a volatile blowing agent is injected into the extruder. To obtain sufficiently finely celled foams, strongly nucleating blowing agents have to be used in an amount of from 2 to 40% by weight, preferably from 6 to 20% by weight, based on the polymer. Suitable are, for example, tetrafluoroethane (HFC 134a), trifluoroethane (HFC 143a) and carbon dioxide, but also sulfur hexafluoride, nitrogen, argon and helium, and also mixtures thereof. In addition, weakly nucleating blowing agents may be used in amounts of from 2 to 40% by weight, based on the polymer, for example hydrocarbons, alcohols, ethers, water and hydrohalocarbons, such as difluoroethane (HFC 152a) and monochlorodifluoroethane (HCFC 142b).

The melt may be further admixed with customary additives, such as nucleating agents, for example talc, flame retardants, colorants, antistats and stabilizers.

The requisite open-cell content is obtained by conducting the extrusion at a comparatively high temperature and/or by using a combination of strongly and weakly nucleating blowing agents, for example combinations of tetrafluoroethane (134a) with difluoroethane (152a) or monochlorodifluoroethane (142b) or of $CO_2$ with difluoroethane.

The invention further provides for the use of flexible open-celled microcellular extruder foams based on thermoplastic polymers for producing fluid-absorbent hygiene articles.

Suitable for this purpose, as well as the abovementioned thermoplastics, are flexibilized styrene polymers, for example styrene-butadiene copolymers, polystyrene impact modified with polybutadiene or polyacrylate rubber, or styrene-acrylonitrile copolymers.

These thermoplastics are as described melt mixed with blowing agents and extruded.

The foams obtained preferably have the following properties:

an open-cell content of more than 40%, preferably more than 50%, a density of less than 300 g/l, preferably of from 20 to 200 g/l, and an average cell diameter of less than 0.5 mm, preferably less than 0.2 mm, especially less than 0.1 mm.

The foams should preferably be surface hydrophilicized for use as hygiene articles. Foam hydrophilicity can be achieved by using hydrophilic (co)polymers, for example acrylic acid, as starting materials or by means of additives during foam production, for example addition of surfactants and/or hydrophilic (co)polymers. However, preference is given to processes where a hydrophilic layer is subsequently generated at the foam surface. Various possibilities are available for this:

By treatment with corona discharge, plasma treatment or by the surface application of ozone.

By surface hydrolysis of the thermplastic copolymers used, for example by hydrolyzing the vinyl acetate in the EVA polymer.

By adsorbing at the foam surface hydrophilicizing components, for example surfactants or hydrophilic polymers with or without a hydrophobic modification.

By chemically attaching hydrophilic reagents to the surface, for example polyamines, such as polyvinylamine or polyethyleneimine; polyepoxides, polycarboxylic acids, such as polyacrylic acid.

By applying a crosslinked hydrophilic sheath either by means of reagents capable of forming a network with themselves, for example addition products of epichlorohydrin with amidoamines.

By applying monomers or polymers capable of reacting with an added crosslinker, for example polycarboxylic acids combined with multifunctional epoxides or polyamines; polyamines combined with multifunctional epoxides, such as polyvinylimine or polyethyleneimine with a bisglycidyl ether of an oligoethylene glycol, also acrylates or esters.

In the examples, percentages are by weight.

EXAMPLE 1

The foam samples were produced by extrusion on a tandem line comprising a ZSK 30 twin screw extruder and a single screw cooling extruder. The polymer and additives are fed to the ZSK 30 (screw diameter 30 mm). The polymer is melted and the blowing agents are mixed in. The melt with its blowing agent is then cooled in the second extruder (screw diameter 60 mm) to the temperature which is necessary for foaming.

The throughput was 10 kg/h and the die had a diameter of 1.5 mm. The blowing agent used was a mixture of monochlorodifluoroethane (HCFC 142b) and tetrafluoroethane (HFC 134a). The polymer was an ethylene-vinyl acetate copolymer (EVA) EVATANE 1040 (VA content: 14%; MFI: 4) from Elf-Atochem. 1.0% of talc was added as nucleating agent.

The results are summarized below in Table 1:

TABLE 1

| Run | 142b (%) | 134a (%) | Melt temp. (° C.) | Density (g/l) | Open-cell content (%) | Cell size (mm) |
|---|---|---|---|---|---|---|
| 1 | 30 | 0 | 80.5 | 39 | 3 | 0.300 |
| 2 | 25 | 5 | 76.2 | 44 | 4 | 0.150 |
| 3 | 20 | 10 | 86.1 | 114 | 76 | 0.040 |

TABLE 1-continued

| Run | 142b (%) | 134a (%) | Melt temp. (° C.) | Density (g/l) | Open-cell content (%) | Cell size (mm) |
|---|---|---|---|---|---|---|
| 4 | 20 | 10 | 85.6 | 154 | 69 | 0.030 |
| 5 | 15 | 10 | 86.3 | 149 | 63 | 0.025 |
| 6 | 15 | 10 | 83.5 | 168 | 60 | 0.020 |

Example 2

Example 1 was repeated except that the polymer used was a copolyester of terephthalic acid, adipic acid and butanediol (ECOFLEX from BASF AG). See Table 2 for results.

TABLE 2

| Run | 142b (%) | 134a (%) | Melt temp. (° C.) | Density (g/l) | Open-cell content (%) | Cell size (mm) |
|---|---|---|---|---|---|---|
| 1 | 12.5 | 0 | 95.6 | 39 | 4 | 0.15 |
| 2 | 7.5 | 5 | 96.3 | 178 | 49 | 0.09 |
| 3 | 5 | 7.5 | 93.0 | 91 | 61 | 0.08 |
| 4 | 2.5 | 10 | 93.4 | 107 | 73 | 0.07 |

Example 3

The EVA foam produced according to run 3 of Example 1 and the ECOFLEX foam produced according to run 3 of Example 2 were cut with a sharp knife to cut out pieces measuring 0.3×5 cm. These were dipped into 1% solutions of various reagents (see Table 2) in isopropanol and briefly evacuated 3 times (until bubbles stopped escaping). The foam pieces were then removed, placed on filter paper to remove excess solution and then dried at 40° C. under reduced pressure in a drying cabinet. The resulting hydrophilicity was tested by applying water droplets to the surface of the foams. Most of the treated samples showed very rapid water absorption (Table 3). This hydrophilicity survived even a single wash with pure water.

TABLE 3

| | | Water absorption | | |
|---|---|---|---|---|
| | | | EVA | |
| No. | Surfactant (1% solution in iso-PrOH) | ECOFLEX | treated | washed |
| 1 | none | − | − | − |
| 2 | Nuwet 100 (fr. OSI) | ++ | ++ | + |
| 3 | Nuwet 300 (fr. OSI ) | + | + | − |
| 4 | Nuwet 500 Finish (fr. OSI ) | ++ | + | + |
| 5 | Cremophor WOCE 5115 (fr. BASF) | ++ | + | +/− |
| 6 | Cremophor A6 (ft. BASF) | ++ | +/− | − |
| 7 | Lutensol LF 400 (fr. BASF) | ++ | ++ | ++ |

++ very rapid;
+ rapid;
+/− slow;
− no absorption, the droplet remains on the surface.

Example 4

The EVA foam produced according to run 3 of Example 1 and the ECOFLEX foam produced according to run 3 of Example 2 were cut with a sharp knife to cut out pieces measuring 0.3×5 cm. These were dipped into a 1% solution of polyvinylamine (K 90) in a 1:1 mixture of water/isopropanol and briefly evacuated 3 times. The foam pieces were then removed, placed on filter paper to remove excess solution and then dried at 40° C. under reduced pressure. The resulting hydrophilicity was tested as in Example 3.

Example 5

The EVA foam produced according to run 3 of Example 1 and the ECOFLEX foam produced according to run 3 of Example 2 were cut with a sharp knife to cut out pieces measuring 0.3×5 cm. A 1% solution of polyvinylamine (K 90) was prepared in a 1:1 mixture of water/isopropanol which had been cooled to 10° C. and 5%, based on the polyvinylamine, of ethylene glycol bisglycidyl ether were added. The foams were dipped into this reaction mixture and briefly evacuated 3 times. The foam pieces were then removed, placed on filter paper to remove excess solution and then dried at 40° C. under reduced pressure. The resulting hydrophilicity was tested as in Example 3.

Example 6

The EVA foam produced according to run 3 of Example 1 and the ECOFLEX foam produced according to run 3 of Example 2 were cut with a sharp knife to cut out pieces measuring 0.3×5 cm. These were dipped into a 1% solution of polyvinylamine (K 90) in a 1:1 mixture of water/isopropanol and briefly evacuated 3 times. The foam pieces were then removed, placed on filter paper to remove excess solution and then dried at 40° C. under reduced pressure. The sample obtained was then dipped into a 1% solution of polyacrylic acid (K 110) in a 1:1 mixture of water/isopropanol and briefly evacuated 3 times. The foam pieces were then removed from the solution, placed on filter paper to remove excess solution and then dried at 40° C. under reduced pressure. The resulting hydrophilicity was tested as in Example 3.

TABLE 4

| | Water absorption | | | |
| | Ecoflex | | EVA | |
| Example | treated | washed | treated | washed |
| --- | --- | --- | --- | --- |
| 4 | ++ | + | ++ | + |
| 5 | ++ | ++ | ++ | ++ |
| 6 | ++ | ++ | ++ | ++ |

We claim:

1. Fluid-absorbent hygiene articles made from flexible, open-celled microcellular extruded foams based on copolymers of ethylene and vinyl acetate or on biodegradable copolyesters of terephthalic acid, adipic acid and butanediol, the foams having the following properties:
   an open-cell content of more than 40%,
   a density of less than 300 g/l, and
   an average cell diameter of less than 0.5 mm.

2. A process for producing the foams of claim 1, which comprises extruding the polymer melt together with from 2 to 40% by weight, based on the polymer, of one or more strongly nucleating volatile blowing agents.

3. A process as claimed in claim 2, wherein the strongly nucleating blowing agents are tetrafluoroethane, trifluoroethane, carbon dioxide, sulfur hexafluoride, nitrogen, argon and/or helium.

4. A process as claimed in claim 2, wherein weakly nucleating blowing agents are used in amounts of from 2 to 40% by weight, based on the polymer, in addition to strongly nucleating blowing agents.

5. The fluid-absorbent hygiene articles of claim 1 which are infant diapers, incontinence products, sanitary protection articles or wound dressings.

* * * * *